United States Patent
Gronau et al.

(10) Patent No.: US 8,991,414 B2
(45) Date of Patent: Mar. 31, 2015

(54) METHOD FOR REMOVING BLOOD FROM AN EXTRACORPOREAL BLOOD CIRCUIT FOR A TREATMENT APPARATUS FOLLOWING TERMINATION OF A BLOOD TREATMENT SESSION, AND APPARATUS FOR PERFORMING SAID METHOD

(75) Inventors: Soeren Gronau, Nauheim (DE); Goetz Guenther, Oberursel (DE); Juergen Haecker, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 799 days.

(21) Appl. No.: 13/148,341

(22) PCT Filed: Feb. 10, 2010

(86) PCT No.: PCT/EP2010/000808
§ 371 (c)(1),
(2), (4) Date: Sep. 20, 2011

(87) PCT Pub. No.: WO2010/091841
PCT Pub. Date: Aug. 19, 2010

(65) Prior Publication Data
US 2012/0000547 A1    Jan. 5, 2012

(30) Foreign Application Priority Data

Feb. 11, 2009 (DE) .......................... 10 2009 008 346

(51) Int. Cl.
*B08B 9/02* (2006.01)
*B08B 3/00* (2006.01)
*A61M 1/36* (2006.01)

(52) U.S. Cl.
CPC ........... *A61M 1/3643* (2013.01); *A61M 1/3646* (2014.02); *A61M 1/3652* (2014.02)
USPC .................. 137/15.04; 134/166 C; 137/15.05

(58) Field of Classification Search
CPC A61M 1/3643; A61M 1/3646; A61M 1/3652
USPC ........................................ 134/166; 137/15.04
See application file for complete search history.

(56) References Cited

U.S. PATENT DOCUMENTS

| 4,517,081 A | 5/1985 | Amiot et al. |
| 5,685,835 A | 11/1997 | Brugger |
| 5,948,251 A | 9/1999 | Brugger |
| 2010/0087772 A1 | 4/2010 | Gronau et al. |

FOREIGN PATENT DOCUMENTS

| DE | 100 11 208 C1 | 9/2001 |
| DE | 102 45 619 A1 | 3/2004 |
| DE | 10 2006 012087 A1 | 9/2007 |
| EP | 1 161 271 B1 | 12/2001 |
| WO | 96/40313 A1 | 12/1996 |
| WO | 01/51106 A1 | 7/2001 |
| WO | 2008/028579 A1 | 3/2008 |

OTHER PUBLICATIONS

International Search Report for PCT/EP2010/000808, mailed on May 31, 2010.

*Primary Examiner* — Dirk Bass
(74) *Attorney, Agent, or Firm* — Kenyon & Kenyon LLP

(57) ABSTRACT

A method for removing blood from an extracorporeal blood circuit of a treatment apparatus for the extracorporeal blood treatment of a patient following termination of a blood treatment session, wherein the treatment apparatus includes at least one extracorporeal blood circuithaving a conduit interior; at least one blood pump for conveying blood inside the conduit interior of the extracorporeal blood circuit; and at least one substitute pumpfor introducing or conveying at least one substituate fluid inside the conduit interior of the extracorporeal blood circuit. The method comprises feeding of air into the conduit interior of the extracorporeal blood circuit by operating the blood pump, and introducing substituate fluid into the conduit interior of the extracorporeal blood circuitby operating the substitute pump. In addition, a suitable apparatus is described.

10 Claims, 1 Drawing Sheet

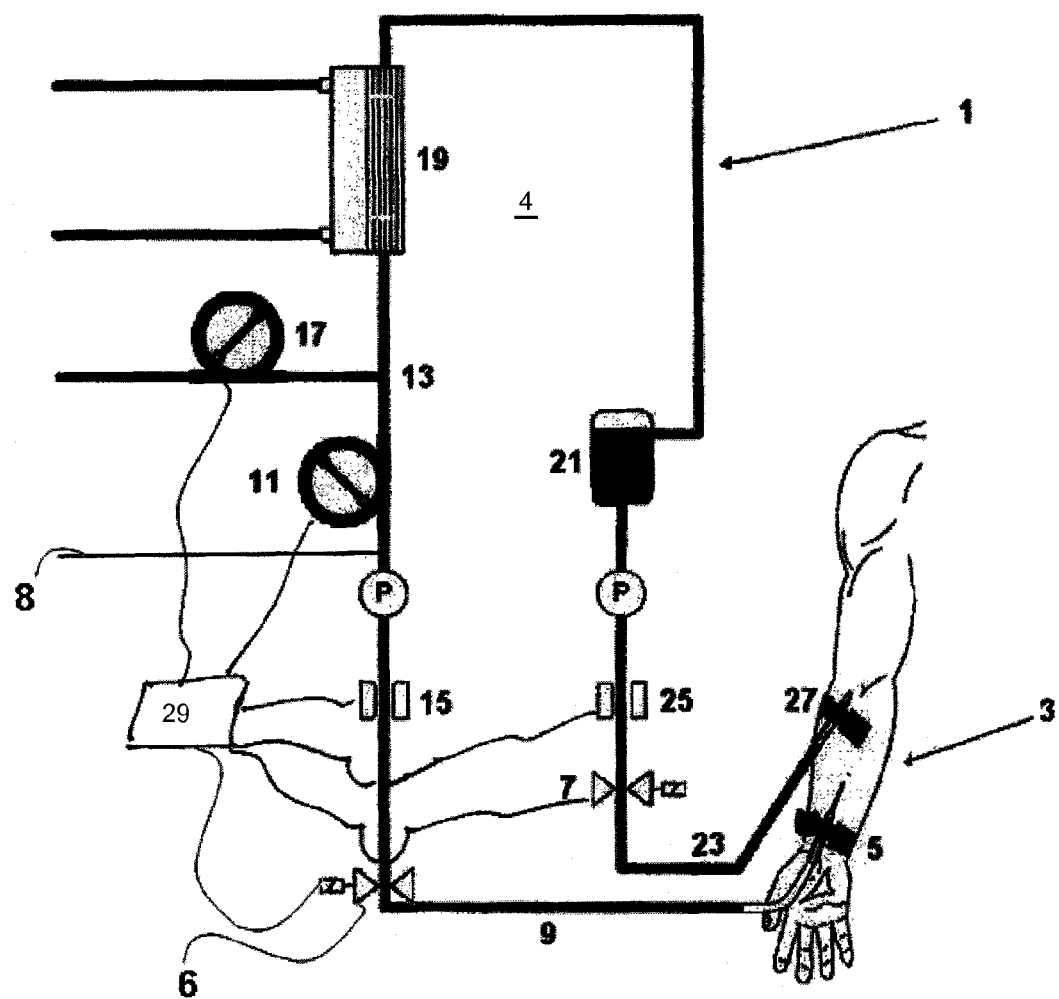

METHOD FOR REMOVING BLOOD FROM AN EXTRACORPOREAL BLOOD CIRCUIT FOR A TREATMENT APPARATUS FOLLOWING TERMINATION OF A BLOOD TREATMENT SESSION, AND APPARATUS FOR PERFORMING SAID METHOD

CROSS REFERENCE TO RELATED APPLICATIONS

This is a 371 national phase application of PCT/EP2010/000808 filed Feb. 10, 2010, claiming priority to German Patent Application No. 10 2009 008 346.4.1 filed Feb. 11, 2009.

FIELD OF INVENTION

The present invention relates to a method for removing blood from an extracorporeal blood circuit for a treatment apparatus for the extracorporeal blood treatment of a patient following termination of the blood treatment session, and an apparatus for performing the method of the present invention.

BACKGROUND OF THE INVENTION

Extracorporeal blood circuits typically are one-way articles and are disposed of after use. Disposal is cost-intensive, with the respective fees being calculated by weight of waste material. For this reason, and moreover in order to reduce a contamination hazard, the blood circuit is therefore emptied of blood prior to its disposal.

To this end it is known from practice and from WO 01/51106 to remove the blood present in an extracorporeal blood circuit following a blood treatment session by introducing air into the extracorporeal blood circuit or into the conduit interior thereof, respectively. This manner of proceeding does, however, harbor the risk of feeding air into the patient's vascular system while the extracorporeal blood circuit is still connected to the patient's vascular system. Moreover this method may give rise to a formation of foam in the range of a blood filter present in the extracorporeal blood circuit, thus making it more difficult to discharge the blood from the extracorporeal blood circuit. Blood remaining inside the extracorporeal blood circuit does, however, in turn constitute a contamination hazard.

SUMMARY OF THE INVENTION

It is an object of the present invention to specify another method as well as a suitable apparatus for removing blood from an extracorporeal blood circuit.

The method of the present invention comprises the feeding or introduction of air and substitute fluid into the extracorporeal blood circuit, for example following termination of a blood treatment session.

Such a "blood treatment session" may, for example, be a unit of treatment by hemodialysis, hemofiltration, hemodiafiltration and/or may be directed to a cell separation method and to the treatment and/or purification of blood. For the performance of such a blood treatment a suitable blood treatment apparatus is used.

A blood treatment apparatus suited for performing the method of the present invention comprises an extracorporeal blood circuit having a conduit interior, various conveying means for introducing and/or conveying various fluids inside the conduit interior of the extracorporeal blood circuit, and for instance a means for treating the patient's blood, such as one or several blood filters and/or one or several dialyzers and/or one or several adsorbers. It may further comprise containers for storing fluids, elements for introducing the fluids such as, e.g., tube elements and/or valves, as well as further means such as, e.g., an air separation chamber for removing air from the blood during the blood treatment, and/or sensors and/or detectors for detecting various relevant parameters such as, e.g., a pressure inside the extracorporeal blood circuit.

An "extracorporeal blood circuit" as mentioned hereinbelow may be configured, e.g., as a tubing system of customary synthetic material and may comprise means for connecting and/or fastening individual portions of the extracorporeal blood circuit to or on further means of the blood treatment apparatus and/or a patient's vascular system, such as, e.g., clamps, access devices to the patient's vascular system such as, e.g., connection needles, feed means through which drugs may be introduced into the conduit interior and/or samples may be taken from the conduit interior for an examination thereof, and the like.

The extracorporeal blood circuit is suited for receiving and conveying fluids in its conduit interior. In the present invention the extracorporeal blood circuit is particularly suited for receiving and conveying a patient's blood as well as air and at least one substituate fluid in its conduit interior. The respective fluids present inside the conduit interior of the extracorporeal blood circuit indicate the content of the "conduit interior of the extracorporeal blood circuit" at the corresponding point of time. The content may preferably be gaseous and/or liquid and include one or several fluids.

Moreover liquids, gases, gases and/or solids dissolved in liquids, suspensions, emulsions, dispersions and other compositions suitable for the purposes of treating a patient's blood may generally form the content of the conduit interior of an extracorporeal blood circuit or be a part thereof.

Conveying means for introducing and/or conveying fluids inside the conduit interior of the extracorporeal blood circuit may be selected in accordance with the employed fluids. Examples include membrane pumps, peristaltic pumps, roller pumps, etc. The "blood pump" may be realized, e.g., as a peristaltic pump or roller pump.

As conveying means for introducing at least one substituate fluid into the conduit interior of the extracorporeal blood circuit and/or conveying a conduit content inside the conduit interior of the extracorporeal blood circuit, a peristaltic pump, e.g., a roller pump, may be employed. It is, however, also possible to employ a different pump type, e.g., a membrane pump, in particular a membrane pump allowing highly accurate metering.

This conveying means may be a "second" conveying means and thus a conveying means that is not identical with the blood pump. The blood pump may, however, also be configured for performing both the typical functions of a blood pump and the function(s) of introducing substituate fluid into the conduit interior and/or conveying a conduit content. Whenever "second" conveying means are mentioned in the following for the sole reason of improved clarity, this should be understood to mean the blood pump or a conveying means different from the latter. Both variants are equally encompassed by the present invention.

Furthermore the second conveying means may be configured with feed lines to various storage means such as storage containers which may contain at least one substituate fluid, and/or may include at least one (closed- and/or open-loop) control means allowing an automated introduction and/or conveying the at least one substituate fluid. The second conveying means may be realized as a roller pump.

The second conveying means and its components, in particular its feed lines into the extracorporeal blood circuit, preferably constitute a part of the tube set for the extracorporeal blood treatment and are provided on or in the extracorporeal blood circuit, in particular by being connected to the latter in a suitable manner, e.g. with the aid of clamps, connecting sleeves, or the like.

Alternatively, the second conveying means may also be present within the extracorporeal blood circuit and suck in substituate fluid via a substituate line.

As was already set forth in the foregoing, the second conveying means may also be embodied by the blood pump.

A substituate line is preferably a feed line which may be connected from a substituate source. The substituate line may be part or accessory of a tube set for the extracorporeal blood treatment. It is, however, not a genuine component of the extracorporeal blood circuit inasmuch as no blood flows through the substituate line.

The method of the present invention comprises the step of introducing or feeding air into the conduit interior of the extracorporeal blood circuit by operating the blood pump. The air may, for instance, be atmospheric air. The present invention is, however, intended not to be restricted to the sole utilization of air but to furthermore encompass any gaseous fluids other than air that are appropriate for the purposes of the present invention.

"Feeding air into the conduit interior of the extracorporeal blood circuit" following termination of the blood treatment session may be effected exclusively or auxiliarly with the aid of the blood pump. Thus it may, e.g., also be possible to additionally inject and/or suck air into the extracorporeal blood circuit with the aid of appropriate means, or to allow air to enter by fluid communication connections with the environment without intervention by mechanical means.

In accordance with the present invention it is also possible to introduce air into the conduit interior of the extracorporeal blood circuit with the aid of the second conveying means for introducing and/or conveying substituate fluid, in particular after substituate fluid was already introduced.

Combinations of the above-mentioned options are also encompassed in accordance with the present invention.

The "introduction of substituate fluid into the conduit interior of the extracorporeal blood circuit" is effected by operating the blood pump and/or the second conveying means.

The blood pump may convey substituate fluid by sucking it in from a feed line to a container for the substituate fluid that opens into the extracorporeal blood circuit between the suction side of the blood pump and a detection means. To this end, e.g., a tube clamp provided in the arterial leg of the extracorporeal blood circuit may be provided.

If the blood pump should feed and convey both blood and substituate fluid into the extracorporeal blood circuit, the method of the present invention may be performed with one pump only. While such a further preferred embodiment is encompassed by the present invention, embodiments employing a blood pump and a second conveying means will be described in the following. The following description is intended to facilitate an understanding of the principles underlying the present invention and of the functions of the single components.

A "substituate fluid" may, for example, be any generally known substituate fluid suitable for use in a blood treatment such as, e.g., a hemodiafiltration, preferably a solution used already during the blood treatment session and thus already incorporated in the extracorporeal blood circuit, or an isotonic saline solution such as, e.g., a 0.9% NaCl solution that may be fed into the extracorporeal blood circuit via a fluid communication.

In accordance with the present invention, the substituate fluid may also be understood as to be a fluid other than a liquid, the use of which is also conceivable in accordance with the present invention.

The substituate fluid may, for example, also be understood as a drug introduced, e.g., by means of a perfusor via an addition point.

Although the present description occasionally refers to a treatment apparatus for a dialysis treatment, the present invention at any rate is not restricted to a performance of the method in order to evacuate the extracorporeal blood circuit following a dialysis treatment. The method of the present invention is rather suited for removing blood from any extracorporeal blood circuit following termination of an extracorporeal blood treatment.

A "patient" within the meaning of the present invention may be either a human or an animal requiring an extracorporeal blood treatment. The "patient's vascular system" presently designates the patient's blood circuit in the sense of an anatomical structure and includes, i.a., fistulae, shunts etc. applied post partum, furthermore arterial and venous conduit structures of the body, and the like.

In the method of the present invention, both air and substituate fluid, or any fluid reasonably useful in the context of the present invention are introduced or fed into the conduit interior of the extracorporeal blood circuit following the termination of a blood treatment session. The substituate fluid may, i.a., preferably have a function of purging the conduit interior in order to prevent a contamination hazard.

It may preferably reduce or prevent a formation of foam, e.g., at the outlet of the blood filter.

The air may, i.a., preferably displace liquids such as blood from the conduit interior of the extracorporeal blood circuit to thus reduce the weight of the extracorporeal blood circuit to be disposed of.

A preferred embodiment in accordance with the present invention comprises the detection of a qualitative change of the content of the conduit interior of the extracorporeal blood circuit with the aid of at least one detection means disposed in a portion of the extracorporeal blood circuit.

The "qualitative change" may refer to one or several areas or portions of the extracorporeal blood circuit, for example an area or portion in which the detection means is present.

A "qualitative change of the content of the conduit interior" includes a change of the composition of the content of the conduit interior, such as, e.g., a change of the single proportions of blood, substituate fluid and/or air inside the conduit interior or a portion thereof, relative to each other. Furthermore the absence of a previously present fluid may constitute a change of composition. A qualitative change may also be a transition, e.g., from a gaseous content to a liquid content, or vice versa. This may, e.g., be a transition from blood to air. Likewise, a qualitative change may be a transition from a first liquid content to a second, different liquid content such as, e.g., a transition from blood to substituate fluid. Such changes may be detected easily, for instance by way of an optical change of the content such as a brightening or darkening of the content.

The "detection means" disposed in a portion of the extracorporeal blood circuit may, e.g., be an optical sensor that detects an optical change of the content of the conduit interior or a characteristic feature of the content. Thus, e.g., a blood/air content inside the conduit interior of the extracorporeal blood circuit is brighter than pure blood due to the oxygen present. Other suitable sensors include pressure sensors for detecting a pressure drop in the event of a change of the content inside the conduit interior, and sensors for detecting a change of density of the content of the conduit interior of the extracorporeal blood circuit, without being restricted thereto.

The "portion of the extracorporeal blood circuit" may be an arterial and/or venous portion of the extracorporeal blood circuit. "Arterial portion" designates a portion of the extracorporeal blood circuit through which blood flows from the patient's vascular system in a direction towards the blood treatment means. "Venous portion" designates the portion of the extracorporeal blood circuit through which blood flows back from the blood treatment means to the patient's vascular system.

The detection means may give information concerning the conditions present at a given moment inside the conduit interior of the extracorporeal blood circuit at a portion thereof. The method of the present invention may thus enable better and more deliberate (closed- or open-loop) control. Moreover it is also possible to dispose several detection means for the detection of same parameters in different portions of the extracorporeal blood circuit and/or to dispose different detection means for the detection of different parameters in the same portions of the extracorporeal blood circuit.

In another preferred embodiment of the method of the present invention, the extracorporeal blood circuit includes at least one access device adapted to be connected to a portion of the patient's vascular system, wherein the method comprises disconnecting the extracorporeal blood circuit from the patient's vascular system, in particular in the area of a first— e.g., arterial—access device, in particular at an end of the extracorporeal blood circuit.

As in the foregoing, such a "portion of the vascular system" may be an arterial and/or venous portion of the extracorporeal blood circuit. Part of such a portion may consist of an "access device adapted to be connected to the patient's vascular system" having the form of a cannula, needle, catheter, etc. and adapted to be connected to the patient's vascular system as needed. Such an access device may be configured as a so-called Double-Needle or Single-Needle variant.

While in the Double-Needle variant one arterial connection needle and one venous connection needle are each connected to the patient's vascular system and to the extracorporeal blood circuit or the arterial and venous portions thereof, the Single-Needle only comprises a connection needle directly connected to the patient's vascular system and a conduit portion subsequently branching in a "Y" shape, the respective "legs" of which are branched into the arterial and venous portions of the extracorporeal portion.

"Disconnecting the extracorporeal blood circuit from the patient's vascular system" designates the interruption of a connection between the extracorporeal blood circuit and the patient's vascular system in a portion of the extracorporeal blood circuit, for example at an end thereof. Such interruption may be effected at either one of the arterial or venous portions, while a disconnection of the arterial portion of the extracorporeal blood circuit being preferred in the present invention.

Disconnecting in the "area of the first access device" may be understood, e.g., as withdrawing the arterial connection needle of a Double-Needle access.

Disconnecting may also be understood as an interruption of the flow connection between the arterial portion of the extracorporeal blood circuit and the arterial connection needle.

In the case of the Single-Needle variant, interrupting the connection may be understood as disconnecting the arterial leg of the "Y"-shaped portion of the extracorporeal blood circuit and the only connection needle that is connected to the patient's vascular system. The open lumen of the arterial leg of the Y-member may be closed in any desired manner (manually, mechanically, automatically, etc.) following its interruption.

As an alternative or in addition, the same may also be applied to the venous portion of the extracorporeal blood circuit and to the venous access to the patient's vascular system.

The selection of the access device with suitable access to the patient's vascular system is not crucial for realizing the present invention. For the sake of simplicity, the present description variously refers to the Double-Needle access, without intending to restrict the present invention thereto. It should be noted that the present invention may equally be realized with a Single-Needle access or any other access device that is appropriate for the purposes of a blood treatment.

Disconnecting the extracorporeal blood circuit allows in a simple and uncomplicated manner to feed or introduce air into the conduit interior of the extracorporeal blood circuit in order to perform the method of the present invention due to a fluid communication with the atmosphere being established via disconnection.

A further preferred embodiment of the present invention encompasses conveying a defined volume of air by operating the blood pump.

In order to convey a "defined volume of air", the blood pump may, e.g., be operated for a time period determined in advance and/or a specific number of revolutions.

"Conveying a defined volume of air" may, however, also correspond to conveying a particular conveying volume of the content and/or to conveying the content across a predetermined conveying distance along the conduit interior of the extracorporeal blood circuit.

A further preferred embodiment of the method of the present invention comprises conveying the "air/blood content" inside the conduit interior of the extracorporeal blood circuit until the "air/blood content" reaches an addition point of the extracorporeal blood circuit for adding substituate fluid into the conduit interior of the extracorporeal blood circuit.

The "air/blood content" may be conveyed, e.g., in a direction away from the disconnected end of the extracorporeal blood circuit.

The "air/blood content" designates the content obtained by introducing air into the extracorporeal blood circuit which already contains blood following the termination of the blood treatment session, wherein blood and air may be the only—or substantially the only—fluids present inside the extracorporeal blood circuit.

An "addition point of the extracorporeal blood circuit for adding substituate fluid into the conduit interior of the extracorporeal blood circuit" may be disposed in the arterial portion and/or venous portion of the extracorporeal blood circuit. In a preferred manner, the "addition point" is disposed in a portion of the extracorporeal blood circuit through which blood flows in a direction away from the disconnected end of the extracorporeal blood circuit. In a particularly preferred manner, the addition point is disposed in the portion of the extracorporeal blood circuit through which blood flows before reaching and passing through the blood treatment means such as, e.g., a blood filter. Such an addition point may be selected appropriately for the addition of substituate fluid in the extracorporeal blood circuit, so that substituate fluid may be introduced, with the aid of the second conveying means, as a kind of separating layer or as a kind of separating volume between the blood volume and the air volume.

Suitable examples for an addition point include an open/close valve, a stop valve, an add-on side line of a branched portion of the extracorporeal blood circuit, etc.

"Conveying the air/blood content" may be effected by operating the blood pump. Once the air/blood content or a formed air/blood boundary or an air/blood transition area or a mixed air/blood area reaches the addition point of the extracorporeal blood circuit for adding substitute fluid into the conduit interior of the extracorporeal blood circuit, conveying the air/blood content may be stopped. This may be achieved by stopping the blood pump. Accurate stopping of conveying the air/blood content may be achieved by introducing a defined volume of air at, or a predetermined distance upstream from, the addition point for substitute fluid.

According to the present invention, "reaching" the addition point should preferably and exemplarily be understood as that the air/blood content is conveyed up to a position in the vicinity or in immediate vicinity of the addition point (merging point, merging area or the like) for the substitute fluid—e.g., upstream from it—or precisely to the position of the addition point for substitute fluid. The expression "reaching" should therefore not be restricted to an absolute "arrival" of the air/blood content at the addition point for substitute fluid. It should rather define a relative or otherwise appropriate position of the conveyed conduit content relative to the addition point for substitute fluid. The full breadth of this definition shall furthermore apply to all of the presently specified embodiments.

Thus, in a preferred embodiment the blood pump may be stopped while the air/blood boundary has not yet reached the addition point, i.e., upstream therefrom. This may advantageously preferably be effected such that no air is conveyed into a blood filter.

The present invention furthermore encompasses an arrangement where the conveying of substitute fluid starts even while the blood pump air is sucking in air, however the air has not yet reached the addition point for substitute fluid.

In this way a "declogging" of the blood filter may advantageously be achieved.

In addition, a further detection means such as, e.g., an air/blood detector having a suitable configuration may be disposed in the said portion of the extracorporeal circuit such as, for instance, the arterial portion of the extracorporeal blood circuit, e.g., between the blood pump and the addition point for substitute fluid, to detect the appearance of air inside the conduit interior of the extracorporeal blood circuit. Such an air/blood detector may in turn be configured as an optical sensor and detect the appearance of air inside the conduit interior of the extracorporeal blood circuit as an optical change of the conduit content.

When the air/blood content reaches the addition point for substitute fluid and/or a detection means detects the appearance of air inside the conduit interior of the extracorporeal blood circuit, substitute fluid is fed or introduced into the conduit interior of the extracorporeal blood circuit at the addition point for substitute fluid by operating the second conveying means, for example a peristaltic or roller pump.

Conveying substitute fluid may preferably already start before the blood pump sucks in air. As an alternative, however, conveyance may preferably also be started while the blood pump is sucking in air.

The substitute fluid fed or introduced into the conduit interior of the extracorporeal blood circuit may be an indefinite amount or a predetermined amount or a limited amount of substitute fluid.

"Introduction of a predetermined amount of substitute fluid" may produce an "air/substitute fluid/blood content." Here, the expression "air/substitute fluid/blood content" means that the substitute fluid is introduced between the blood conveyed by the extracorporeal blood circuit and the air conveyed by the extracorporeal blood circuit, to thus form a kind of "buffer" between air and blood.

A "predetermined amount of substitute fluid" may correspond to a particular conveying volume and/or a particular conveying distance of the content along the conduit interior of the extracorporeal blood circuit and may be effected, e.g., by operating a membrane pump allowing highly accurate metering.

The amount of substitute fluid may preferably be predetermined as a quantity, for example as a volume of a predetermined measurement quantity and unit. The absolute quantity of the amount of substitute fluid may preferably be stored or input in, for example, a control means of the apparatus of the present invention. The amount of substitute fluid, within the scope of technical accuracy, may preferably be conveyed exactly.

In order to predetermine an exact amount of substitute fluid, it is for example possible to store or input technical specifications of the extracorporeal blood circuit used, such as, e.g., the inner volumes of the tube set, in the control means. With the aid of the technical specifications of the single components of the extracorporeal blood circuit it is possible, e.g., to calculate a required conveying period and/or a conveying volume.

A "limited amount of substitute fluid" may be an amount of substitute fluid selected, e.g., by way of empirical values on the part of the operating personnel. In a preferred manner, a limited amount of substitute fluid may be introduced and conveyed for such a long time until the appearance of substitute fluid is detected at another detection means inside the conduit interior of the extracorporeal blood circuit. A limited amount of substitute fluid does therefore not have to be known accurately and/or correspond to a particular conveying volume. A limited amount of substitute fluid may, however, be determined indirectly as being "limited" by the inner volumes of the components of the extracorporeal blood circuit through which the amount of substitute fluid flows, in particular the inner volume of the portion from the addition point for substitute fluid and/or the blood treatment means up to another detection means, and by the detection of the substitute fluid by the latter in connection with an interruption of feeding any further substitute fluid. The volume is thus determined in the sense of "limited" without, however, being accurately known, and without a possibility of being indicated in milliliters, for instance, and/or without being stored or input in a control means. The introduction of a limited amount of substitute fluid may be advantageous, for example, when the filter type of a blood treatment apparatus or the capacity of the apparatus is not known or is not specified correctly.

The substitute fluid may be introduced from a dedicated storage container, via corresponding conduit systems of the extracorporeal blood circuit, at the addition point for the substitute fluid in the extracorporeal blood circuit.

The "air/substitute fluid/blood content" produced in this way may be conveyed in a direction away from the disconnected end by operating the blood pump and/or by operating the second conveying means.

Following the introduction of substitute fluid and thus the production of the "air/substitute fluid/blood content", additional air may furthermore be introduced into the conduit interior of the extracorporeal blood circuit. This may in particular be effected by operating the blood pump and/or by operating the second conveying means. Sucking in and introducing air by operating the second conveying means may, for example, be effected by establishing a connection between the suction side of the second conveying means and an exterior of the extracorporeal blood circuit, e.g., the atmosphere.

The further introduction of air may in particular serve for the purpose of substantially eliminating fluids present inside the conduit interior of the extracorporeal blood circuit, in particular blood and substitute fluid, or to reduce the amounts thereof present inside the conduit interior.

Conveying the "air/substitute fluid/blood content" may be stopped, for example, when the detection means detects substitute fluid inside the conduit interior of the extracorporeal blood circuit.

The "detection means" is as defined above and may, for example, be disposed in the venous portion of the extracorporeal blood circuit, e.g., between the blood treatment means and the venous access device to the patient's vascular system, and in particular between a drip chamber in the venous portion and the venous access device.

The detection means may detect the appearance of substituate fluid in a specific portion of the conduit interior of the extracorporeal blood circuit, for example through an optical change of the content of the conduit interior.

Conveying the "air/substitute fluid/blood content" may be stopped when the detection means detects the appearance of air or substitute fluid in the conduit interior of the extracorporeal blood circuit.

This may be effected by stopping the second conveying means.

In a further embodiment of the method of the present invention it is moreover preferred to dispose the detection means at a predetermined distance from a second access device and to convey the content of the conduit interior across the predetermined distance to the access device after air was detected at the detection means.

Without being restricted thereto, the "second access device" may be a venous connection needle of a Double-Needle access or a "venous" leg of a Y-member.

When air is detected by the detection means, the "air/substitute fluid/blood content" may be conveyed across the predetermined distance up to the second access device to thus remove blood, and optionally also substitute fluid, from the extracorporeal blood circuit. Here it is possible to either merely discharge the blood from the extracorporeal blood circuit, or to concurrently return it into the patient's vascular system.

In a further preferred embodiment of the method of the present invention, the blood contained inside the conduit interior of the extracorporeal blood circuit is returned—in particular substantially completely—via the second access device in the patient's vascular system. The expression "returned substantially completely" means that the blood present inside the conduit interior of the extracorporeal blood circuit is removed from the extracorporeal blood circuit nearly without any residues. The residues possibly left in the extracorporeal blood circuit due to technical reasons such as wetting properties, or blood residues left in the drip chamber, should be considered to be as small as to be negligible.

"Returning blood into the patient's vascular system" may take place while an end of the extracorporeal blood circuit such as, for example, the end of the venous portion, e.g., the venous connection needle, is connected to the patient's vascular system. This connection may be maintained or re-established following termination of the blood treatment session.

In addition, it may be further preferred to also remove the substitute fluid—in particular substantially completely—from the conduit interior of the extracorporeal blood circuit. This may be achieved by conveying the content of the conduit interior of the extracorporeal blood circuit merely across the predetermined distance between the detection means and the access device after the detection means detected the appearance of air. The predetermined distance may be correlated with the defined conveying volume of air fed by the blood pump.

The "substantially complete removal" of the substitute fluid from the conduit interior of the extracorporeal blood circuit may equally be considered to virtually not leave any residues as was set forth above with regard to the blood contained inside the conduit interior.

In accordance with the present invention, however, a complete or virtually complete removal is not necessary in order to obtain advantages.

Following the patient's complete (arterial and venous) disconnection and following the restoration of blood to the patient it might optionally be possible to furthermore carry out one of the known (semi-)automated methods for more or less completely evacuating the blood tube set. Such methods convey liquid residues, e.g., into the so-called rinse port of the dialysis machine. It is, of course, possible to convey the residual liquid into any desired outlet port. Such evacuation methods may follow the method of the present invention or be part of an embodiment thereof. They are, however, not required for carrying out the present invention.

Such an apparatus includes at least one extracorporeal blood circuit having a conduit interior, at least one blood pump disposed on or in the extracorporeal blood circuit for conveying blood inside the conduit interior of the extracorporeal blood circuit, at least one—optionally additional—second conveying means provided with a connection to the extracorporeal blood circuit for introducing at least one substitute fluid into the conduit interior and/or for conveying a conduit content inside the conduit interior of the extracorporeal blood circuit, and at least one (closed- or open-loop) control means enabling the performance of a method according to the present invention.

Such a (closed- or open-loop) control means may be configured correspondingly for performing a method of the present invention and may optionally include further means such as, e.g., memory means, feed means, automated signalling means, etc.

As the method of the present invention described in the foregoing may be carried out by using the apparatus of the present invention, reference is made to the above-described embodiments in order to avoid repetitions.

An embodiment of the apparatus of the present invention relates to arranging of at least one detection means for detecting at least one change of the content of the conduit interior of the extracorporeal blood circuit or a characteristic feature of the content in a portion of the extracorporeal blood circuit. A characteristic feature of the content may be a composition, a physical, chemical or biological quantity, for instance a transparency, a pH value, and the like. Such a detection means may correspond to the one described in the foregoing, so that reference is made to the above description thereof in order to avoid repetitions. Vice versa, the definition of the second detection means may unrestrictedly also be correct for any other detection means encompassed in the present disclosure.

The apparatus of the present invention may include additional means that are appropriate for performing the method of the present invention and/or other means for performing a blood treatment such as, for example, a blood treatment means, e.g., a blood filter, an alarm means, "emergency stop" means, and the like.

Each one of these means may be both disposed in the extracorporeal blood circuit and connected to it. The feed lines and/or ports, fastening means and the like that are appropriate for this purpose may equally be encompassed by the apparatus of the present invention.

Without being restricted thereto, an apparatus of the present invention may be suited for performing a hemodialysis, a hemofiltration, a hemodiafiltration, and separation methods.

It should be noted that the present invention is not limited to the above-described embodiments of the apparatus of the present invention. Moreover any other treatment apparatuses allowing for performance of the method of the present invention are also encompassed by the present invention.

The present invention may advantageously be employed for removing blood from the extracorporeal blood circuit for a treatment apparatus for an extracorporeal blood treatment of a patient following termination of a blood treatment session: As air and substitute fluid are concurrently present in the form of an air/substitute fluid/blood content inside the conduit interior of the extracorporeal blood circuit following termination of the blood treatment session, it is possible to remove the blood present inside the conduit interior of the extracorporeal blood circuit from the extracorporeal blood circuit. This may be achieved without any risk of introducing air into the patient's body.

In addition, it is possible to prevent a contamination hazard in the further handling or disposal of the extracorporeal blood circuit.

Moreover it is possible to reduce the gross waste material weight of the extracorporeal blood circuit which is, after its utilization in a blood treatment session, made up of blood circuit material and liquid blood circuit content. As the fees for disposal of an extracorporeal blood circuit are calculated by weight, it is thus advantageously possible to save costs.

By conveying amounts of air and substitute fluid in particular defined by volume, the content of the conduit interior of the extracorporeal blood circuit may be conveyed across predetermined distances in the extracorporeal blood circuit, wherein a substantial removal of liquids (blood and optionally also substitute fluid) from the conduit interior of the extracorporeal blood circuit can be ensured. Here only a small amount of substitute fluid is required, whereby the costs and the provisioning expense for the substitute used are advantageously reduced.

The amount of substitute fluid optionally remaining in the blood tube set may, for example, correspond to the volume of the venous portion of the extracorporeal blood circuit and amount to as little as, e.g., about 30 ml. This advantageously already contributes to the reduction of the waste material weight of the extracorporeal blood circuit. The amount of substitute fluid remaining in the blood tube set—which is negligible in regard of its contribution to the total weight of the tube set—may advantageously serve as a safety buffer and remain in the blood tube set for this purpose. In this way, it may prevent an introduction of air into the patient's blood circuit.

The introduction of substitute fluid between the air/blood content inside the conduit interior may advantageously contribute to avoiding an introduction of air into the patient's vascular system if the extracorporeal blood circuit is evacuated while being connected to the patient. It is yet possible to purge blood residues from the conduit interior of the extracorporeal blood circuit by using the substitute fluid functioning as a purging liquid, wherein a contamination hazard can thus be precluded. The extracorporeal blood circuit may thus be disposed of safely and at a low residual total weight or gross weight of waste material.

The introduction of substitute fluid may further contribute to cleansing blood from a blood filter having different capillary inner diameters, which, due to the lower pressure drop across the capillaries already filled with air in comparison with the capillaries still filled with blood, might in technical terms hardly be achieved by merely passing air through the filter.

In addition it may also be possible to minimize the formation of foam, e.g. at the outlet of the blood filter, by utilizing substitute fluid there and thus in particular a liquid instead of only a gas (e.g., air) for the purposes of displacing blood or evacuation.

As the method of the present invention may be performed immediately after the termination of a blood treatment session, it may be performed in a simple and easy way while not requiring any technically complex, time-consuming and/or cost-intensive steps.

The method of the present invention may advantageously be performed by using the substitute fluid which is at any rate used or present in a blood treatment, such as, e.g., an isotonic saline solution, e.g., a 0.9% NaCl solution. This in turn advantageously contributes to saving costs and time.

Moreover the method of the present invention may enable to remove blood from the arterial portion of the extracorporeal blood circuit and in particular from the arterial connection needle, and to return the blood into the patient's vascular system. Advantageously it is thus possible to circumvent the step of retrogradely pressing out the blood present in the arterial connection needle, e.g., with the aid of a syringe filled with a saline solution.

The method of the present invention may thus offer the advantage to reintroduce substantially any blood present inside the conduit interior of an extracorporeal blood circuit after its utilization in a blood treatment into the patient.

BRIEF DESCRIPTION OF THE DRAWINGS

In the following, the method of the present invention will be described by way of preferred embodiments with reference to FIG. 1.

FIG. 1 shows a schematic overview of an exemplary arrangement for performing the method of the present invention.

DETAILED DESCRIPTION OF THE DRAWINGS

FIG. 1 represents an extracorporeal blood circuit 1 of an apparatus 4, which has a Double-Needle access to the vascular system of the patient 3. The extracorporeal blood circuit 1 is disconnected from the vascular system of the patient 3 by withdrawing an arterial connection needle 5 from the patient's arm.

In order to start the method of the present invention according to a first embodiment, initially a venous patient hose clamp 7 is opened. Then a blood pump 11 is started and thus air is sucked into an arterial portion 9 of the extracorporeal blood circuit 1. The blood pump 11 is exemplarily configured as a roller pump and feeds a—e.g., predetermined—volume of air into the extracorporeal blood circuit 1 via the disconnected end. Subsequently, the air/blood content is conveyed along the conduit interior of the extracorporeal blood circuit 1 in a direction towards a venous connection needle 27 by operating the blood pump 11.

In this embodiment, the predetermined volume of air is defined such that the air/blood boundary inside the conduit interior of the extracorporeal blood circuit 1 is stopped as accurately as possible upstream of the addition point 13 for substitute fluid. In order to enhance the accuracy of stopping the air/blood boundary upstream of or at the addition point 13 for substitute fluid, an arterial air/blood detector 15 may be positioned in a suitable location inside the arterial portion 9 of the extracorporeal blood circuit 1 between the addition point 13 for substitute fluid and the arterial connection needle 5.

When the air/blood boundary reaches the addition point 13 for substitute fluid, the blood pump 11 is stopped. The second conveying means, which is a substitute pump 17 herein exemplarily configured as a roller pump, feeds a—preferably predetermined—volume of substitute fluid into the conduit interior of the extracorporeal blood circuit 1 via the addition point 13 for substitute fluid. The substitute pump 17 may then be stopped.

As an alternative, the substitute fluid may also be introduced by operating the blood pump 11. To this end, the arterial patient hose clamp 6 is closed and substitute fluid is introduced via a feed line 8 from a storage container for the substitute fluid into the extracorporeal blood circuit 1.

The air/substitute fluid/blood content thus produced is conveyed along the conduit interior of the extracorporeal blood circuit 1 by operating the blood pump 11 again and pushed or conveyed through a blood filter 19, a venous air separation chamber 21, and a venous portion 23 of the extracorporeal blood circuit 1, to thus remove the blood from the extracorporeal blood circuit 1 in a direction towards the venous connection needle 27. It is in turn possible to introduce air by operating the blood pump 11 and/or the substituate pump 17 once again.

Inside a venous portion 23 of the extracorporeal blood circuit a venous air/substitute fluid/blood detector 25 is disposed which detects the appearance of substitute fluid at a predetermined position of the conduit interior of the extracorporeal blood circuit 1.

The blood pump 11 continues to convey the air/substitute fluid/blood content until the blood in the venous portion 23 of the extracorporeal blood circuit has been removed from the same and returned into the vascular system of the patient 3 via the venous connection needle 27 and/or until the appearance of air inside the conduit interior is detected at the venous air/substitute fluid/blood detector 25. The conveying operation of every pump is stopped. An optical and/or acoustic signal may be output.

Control of the apparatus 4 may be effected by the use of a (closed- or open-loop) control means 29.

A second embodiment of the present invention substantially corresponds to the above-described first embodiment, with the difference that the air/substitute fluid/blood content inside the conduit interior of the extracorporeal blood circuit 1, after addition of the substitute fluid, is conveyed along the conduit interior of the extracorporeal blood circuit 1 by operating the substitute pump 17 instead of operating the blood pump 11.

The present invention is not restricted to the above-described embodiments which are merely for illustrative purposes. Furthermore the present invention is not restricted to evacuating the content or parts thereof while maintaining a connection with the vascular system.

The invention claimed is:

1. A method for removing blood from an extracorporeal blood circuit of a treatment apparatus for the extracorporeal blood treatment of a patient following termination of a blood treatment session, wherein the treatment apparatus comprises:

At least one extracorporeal blood circuit having a conduit interior;

At least one blood pump for conveying blood inside the conduit interior of the extracorporeal blood circuit;

At least one conveying means for introducing at least one substitute fluid into the conduit interior of the extracorporeal blood circuit, for conveying a conduit content inside the conduit interior of the extracorporeal blood circuit, or both, said method comprising:

Introducing air into the conduit interior of the at least one extracorporeal blood circuit with the at least one blood pump;

Introducing a substitute fluid into the conduit interior of the at least one extracorporeal blood circuit with the at least one conveying means;

Conveying an air/blood content inside the conduit interior of the extracorporeal blood circuit until at least one of an air/blood boundary reaches an addition point of the extracorporeal blood circuit, or a first detection means for detecting the appearance of air inside the conduit interior detects the appearance of air inside the conduit interior, wherein the first detection means is disposed in a portion of the extracorporeal blood circuit; and Then introducing the substitute fluid into the conduit interior of the extracorporeal blood circuit via the addition point.

2. The method according to claim 1, wherein the treatment apparatus further comprises at least one second detection means disposed in a portion of the extracorporeal blood circuit, said method comprising:

Detecting a qualitative change of the contents of the conduit interior of the extracorporeal blood circuit with the at least one second detection means.

3. The method according to claim 1, wherein the extracorporeal blood circuit comprises at least a first access device adapted to be connected to a portion of a vascular system of the patient, the method further comprising:

disconnecting a portion of the extracorporeal blood circuit from the vascular system of the patient.

4. The method according to claim 1, wherein the air comprises a defined volume of air.

5. The method according to claim 1, wherein the substitute fluid comprises a predetermined amount of substitute fluid.

6. The method according to claim 1, further comprising:

Conveying an air/substitute fluid/blood content along the conduit interior in a direction away from a disconnected portion of the extracorporeal blood circuit until at least one second detection means detects the substitute fluid inside the conduit interior of the extracorporeal circuit.

7. The method according to claim 6, wherein the air/substituate fluid/blood content is conveyed along the conduit interior of the extracorporeal blood circuit by operating the at least one blood pump, the at least one conveying means, or both.

8. The method according to claim 1, further comprising:

introducing the substitute fluid at least at a first time point; and introducing the air at least at a second time point temporally different from said first time point.

9. The method according to claim 2, wherein the extracorporeal blood circuit further comprises a first access device and a second access device, said at least one second detection means being disposed at a predetermined distance from the second access device, said method further comprising:

Conveying the content of the conduit interior of the extracorporeal blood circuit across the predetermined distance to the second access device after air is detected at the at least one second detection means.

10. The method according to claim 9, wherein blood contained inside the conduit interior of the extracorporeal blood circuit is introduced into the vascular system of the patient via the second access device.

* * * * *